United States Patent
Villarreal Guerra et al.

(10) Patent No.: US 9,625,432 B2
(45) Date of Patent: Apr. 18, 2017

(54) ARTIFICIAL OLFACTORY METHOD AND SYSTEM

(71) Applicant: INSTITUTO TECNOLOGICO Y DE ESTUDIOS SUPERIORES DE MONTERREY, Monterrey (MX)

(72) Inventors: Blanca Lorena Villarreal Guerra, Monterrey (MX); Jose Luis Gordillo Moscoso, Monterrey (MX)

(73) Assignee: INSTITUTO TECNOLOGICO Y DE ESTUDIOS SUPERIORES DE MONTERREY, Monterrey (MX)

( * ) Notice: Subject to any disclaimer, the term of this patent is extended or adjusted under 35 U.S.C. 154(b) by 109 days.

(21) Appl. No.: 14/652,025

(22) PCT Filed: Nov. 28, 2013

(86) PCT No.: PCT/MX2013/000151
§ 371 (c)(1),
(2) Date: Jun. 12, 2015

(87) PCT Pub. No.: WO2014/092527
PCT Pub. Date: Jun. 19, 2014

(65) Prior Publication Data
US 2015/0308999 A1   Oct. 29, 2015

(30) Foreign Application Priority Data
Dec. 12, 2012 (MX) .................. MX/a/2012/014508

(51) Int. Cl.
*G01N 33/00* (2006.01)
(52) U.S. Cl.
CPC ..... *G01N 33/0031* (2013.01); *G01N 33/0001* (2013.01)
(58) Field of Classification Search
CPC .................. G01N 33/0001; G01N 33/0031
See application file for complete search history.

(56) References Cited

U.S. PATENT DOCUMENTS 3,885,550 A * 5/1975 MacLeod ........... G01N 33/0001
                                                            600/303
6,467,332 B1 * 10/2002 Bertschi ............. G01N 33/0001
                                                            73/23.34
(Continued)

FOREIGN PATENT DOCUMENTS

CN        201233255 Y        5/2009
CN        201527429 U        7/2010

OTHER PUBLICATIONS

Masahiro Imahashi, Masahi Watanabe, Sunil Kumar Jha, Kenshi Hayashi; Olfactio-inspired Sensing Using a Senor System with Molecular Recognition and Optimal Classification Ability for Comprehensive Detection of Gases, Mar. 12, 2014, www.mdpi.com/journal/sensors, ISSN 1424-8220.*

(Continued)

*Primary Examiner* — Francis Gray
(74) *Attorney, Agent, or Firm* — Baker & McKenzie LLP

(57) ABSTRACT

The invention is a biologically inspired artificial olfactory method and system comprising the design of at least one septum with at least two nostrils, wherein each nostril is designed having special characteristics. This artificial nose permits detecting the direction wherefrom a smell emanates. The septum is utilized to realize the separation of the air currents external to the olfactory system. In this manner the measurement of the environment may be obtained in two different positions simultaneously. These measurements reflect different concentrations and reaction times, consequently they may be utilized to calculate the direction wherefrom a smell emanates.

Each nostril comprises an air chamber performing the principal biological processes carried out within the nose. These processes are: the process of aspiration, the process of (Continued)

division, the process of conduction, the sensing, the processing, the transformation of the air or smell filtration, and expulsion.

27 Claims, 4 Drawing Sheets

(56) References Cited

U.S. PATENT DOCUMENTS

| | | | | |
|---|---|---|---|---|
| 6,703,241 | B1* | 3/2004 | Sunshine | G01N 33/0006 |
| | | | | 436/147 |
| 2006/0191319 | A1* | 8/2006 | Kurup | G01N 33/24 |
| | | | | 73/23.34 |
| 2009/0187111 | A1* | 7/2009 | Reilly, Jr. | A61B 5/097 |
| | | | | 600/532 |
| 2012/0151993 | A1 | 6/2012 | Brasfield | |
| 2013/0263644 | A1* | 10/2013 | Dufour | G01N 33/0016 |
| | | | | 73/23.2 |

OTHER PUBLICATIONS

International Search Report and Written Opinion, PCT/MX2013/000151, dated Apr. 3, 2014, 22 pages.
Villarreal, et al., "Integration of Directional Smell Sense on an UGV", Advances in Artificial Intelligence, Oct. 17, 2012, vol. 7629, pp. 273-284, ISBN 978-3-642-37806-5.
Lilienthal, "A Stereo Electronic Nose for a Mobile Inspection Robot", 1st IEEE International Workshop on Robotic Sensing 2003, Sensing and Perception in 21st Century Robotics, 2003, pp. 1-6.
International Search Report, PCT/MX2013/000151, dated Apr. 3, 2014, 6 pages.

* cited by examiner

ARTIFICIAL OLFACTORY METHOD AND SYSTEM

This patent application is a national phase filing under section 371 of PCT/MX2013/000151, filed Nov. 28, 2013, which claims the priority of Mexican patent application MX/a/2012/014508, filed Dec. 12, 2012, each of which is incorporated herein by reference in its entirety.

TECHNICAL FIELD

The present disclosure relates, according to some embodiments, to artificial olfactory methods and systems to simulate the biological behavior of an olfactory system in such manner that it may be utilized to differentiate different types of smells, concentrations and the direction wherefrom the same emanate. This is achieved by virtue of the implementation of a septum dividing the proximate environment into different zones simultaneously and conducting the air with the concentration of smell from these points to different nostrils. Each nostril performs the biological processes involved in a nose, from the ventilation and desaturation of the sensors to homogenization and filtration, presenting as an advantage a better characterization of the environment and permitting the employment of the system in applications such as, inter alia, the search for sources of smell possibly hazardous to health, search for explosives in disaster zones, following scent trails.

BACKGROUND

In the literature or the state of the art there are to be found devices realizing actions similar to the artificial olfactory system; however the olfactory method and system proposed presents different characteristics rendering it unique with respect to the others. Said differences are described below:

The document CN 201233255 Y, denominated 'Bionic smell system for robot', reveals an olfactory bionic system for a robot comprising a nasal cavity, a system of inspiration and an integrated circuit, all within a casing, and a liquid crystal screen and a control panel assembled on the casing. The nasal cavity is sealed and is formed by an upper cavity board, a lower cavity board and a clapboard located between the upper cavity board and the lower cavity board, forming two air chambers. Each air chamber has an air inlet; the lower chamber presents orifices serving to install the sensors sealed with sealing rings, the clapboard dividing both chambers having the same number of orifices, as a consequence whereof the samples of air entering the chamber and reaching the sensors correspond one-to-one with the position of the air orifices in the clapboard.

The device referred to utilizes the air chambers to isolate it from the integrated circuits; although it has 2 air chambers and a clapboard, differing from the artificial olfactory system, it utilizes solely one of the air chambers to realize the measurements of the environment. In the case of the artificial olfactory system the air chambers are independent and by means of the design of a septum measurements are obtained from different positions in the environment, that is to say of the exterior of the system and not of the interior. Additionally, in the document 'Bionic smell system for robot', the processor and the control panel are integrated into the olfactory bionic system. In contrast, the artificial olfactory system realizes the acquisition of data and sends it wirelessly to any type of processor in order to realize all types of algorithm control and implementation.

Furthermore, the system of aspiration in the olfactory bionic system is utilized solely to carry the air towards the sensors; in contrast, in the biologically inspired artificial olfactory system, the system of inspiration comprises two stages corresponding to the process of inhalation and the process of exhalation. In addition, each air chamber separately disposes of a system of inhalation which simultaneously realizes the homogenization and sampling of the air, in addition to disposing of the inverse mechanism or that of exhalation to desaturate the sensors and prepare them for a further measurement. On inhalation and exhalation it passes through a system of particle filtration, in order to respectively clean the environment and the air chambers.

In the state of the art there is also to be found the document 'Gas collection, ventilation and closing device of electronic nose system' with patent number CN 201527429, revealing a collection, ventilation and closure device of an electronic nose system comprising a sealed body in four layers and 3 compartments, wherein the first layer has a feed port the sample which reaches the first compartment and comprises an admission valve and a discharge valve, the second layer serves to seal the system and wherein the second compartment there is disposed the signal from the matrix of sensors, and in the third layer there is to be found the array of sensors incorporated and encapsulated in the 'electronic nose' system. Finally, the third compartment is the air chamber wherein the sample is collected. This device isolates, in the same manner as the foregoing one, the matrix of sensors of the electronic nose system from the external environment and ensures employing solely the sample to analyze the smell. In addition, this device disposes of a system which on being isolated from the environment, accelerates the recovery and response time of the sensors.

The aforementioned device, differing from the artificial olfactory system, completely isolates the sample and the sensors from the external environment, not being recommendable to obtain the direction wherefrom a smell emanates by virtue of the fact that this depends directly on the environment. The system of smell collection is utilized for other types of application, such as quality control of foods, for example. In contrast, the artificial olfactory system presents a mobile application; this signifies that it may be installed on a type of mobile platform such as, for example, a robot, and specify the direction wherefrom a smell emanates in order that the platform may follow a trajectory and locate possible sources of smell.

DETAILED DESCRIPTION

The olfactory biological system in the human being comprises different processes prior to and subsequent to the smell reaching the olfactory sensors. Consequently, the artificial olfactory method and system, object of this patent application, simulates these processes such that the sample of smell reaching the sensors is the most representative of the environment in that specific position and, in this manner, improves the perception thereof. In this manner, the artificial olfactory method and system comprises a device denominated artificial nose, presenting in turn systems of division of the air, ventilation, conduction, homogenization, sensing, filtration and transformation of smells participating in the method of operation of the artificial olfactory system. These systems permit the desaturation of sensors and improve the measurement. Having realized these processes, the direction wherefrom the smell analyzed emanates is determined, displaying the result on a graphical interface. The proposed system is described below in detail.

Figure 1:
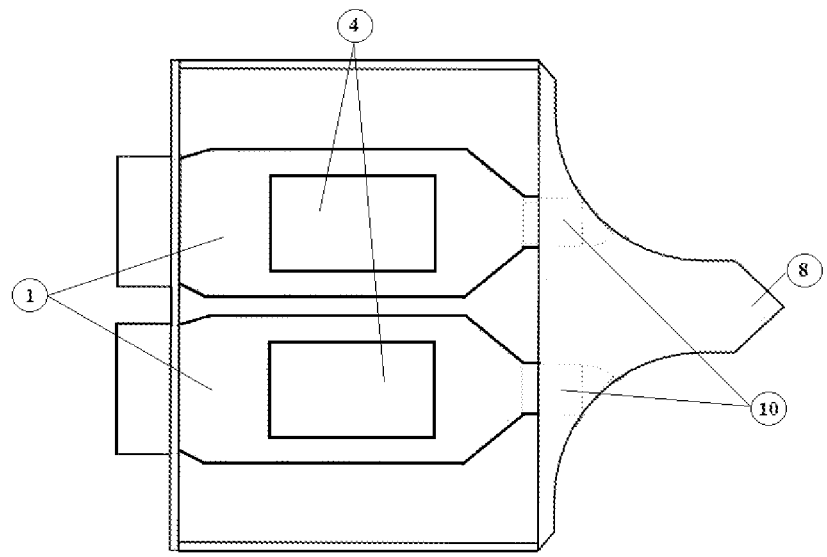
FIG. 1. Plan view of the artificial olfactory system.
Figure 2:
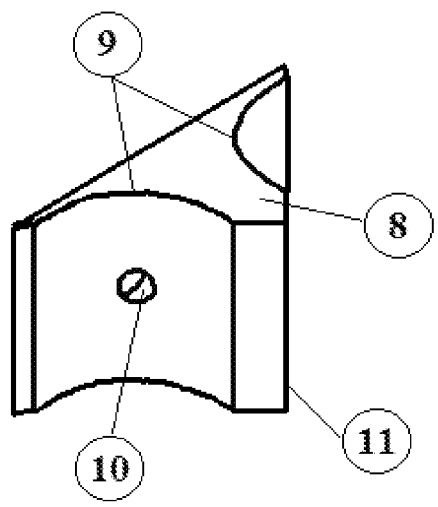
FIG. 2. Isometric view of the divider device or septum.
Figure 3:
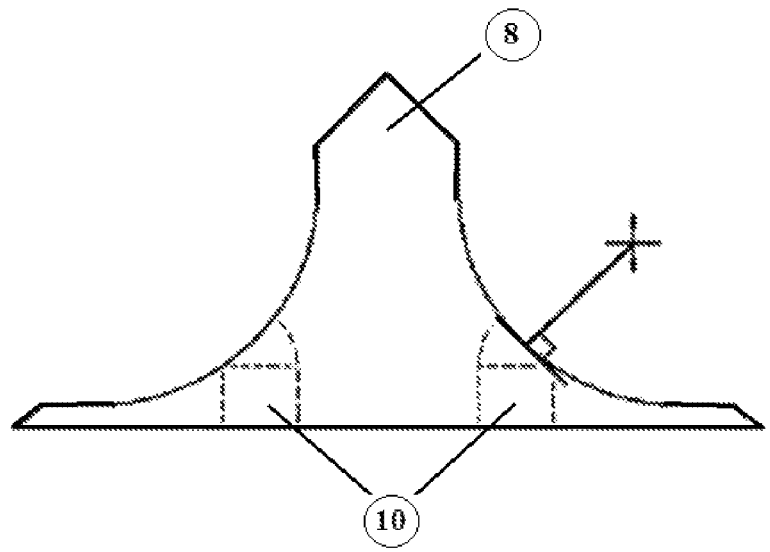
FIG. 3. Plan view of the divider device or septum.

The artificial olfactory system is shown in FIG. 1 and comprises a device denominated artificial nose of non-porous material, preferably plastic in order that it be light, formed by at least two air chambers [1] representing the nostrils, preferably joined, at their posterior part, to least one septum [8]. The septum [8] (see FIGS. 2 and 3) is a single part defined by a geometry similar to the human nasal septum; the septum [8] comprises at least two concave inlets [9], reciprocally opposed, having the objective of permitting the admission of a sample of air from different zones of the environment by virtue of a divider [11] therebetween. In the interposition of the concave inlets [9], and perpendicular thereto, there are channels denominated ducts of the septum [10] passing completely through the septum [8]. The concave shape of the inlets [9] permits that the air be concentrated in the central zone of each of the inlets of the ducts of the septum [10], yielding as a result that the air which enters the air chambers [1] is the most representative of the environment in that position.

Figure 4:
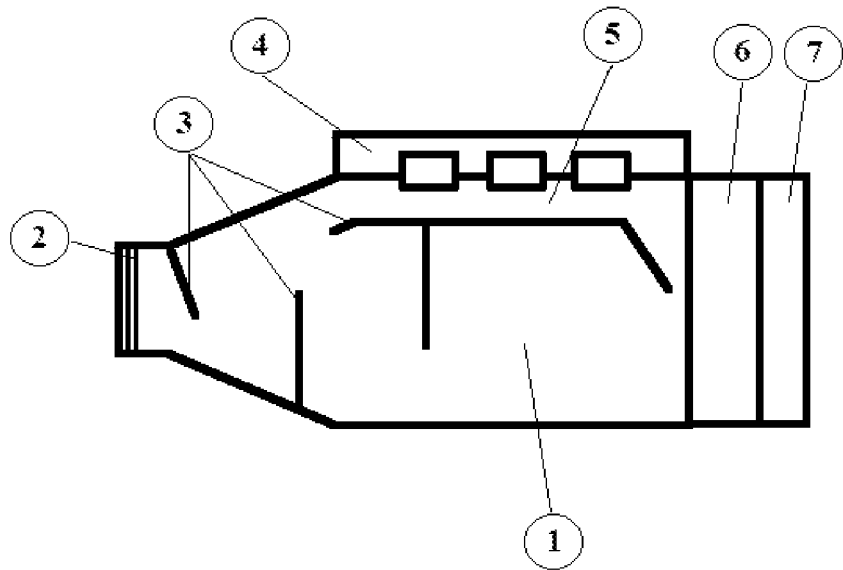
FIG. 4. Side elevation of an air chamber or nostril.
Figure 5:
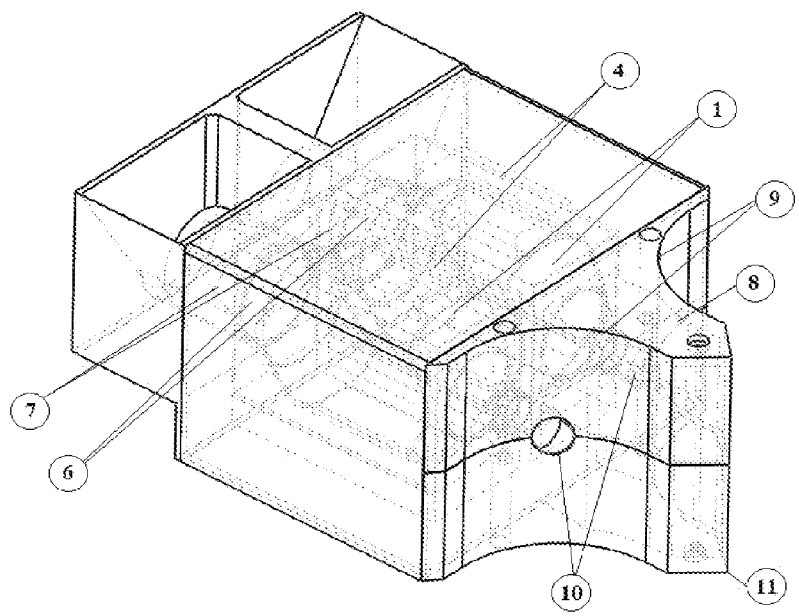
FIG. 5. Isometric view of the artificial olfactory system.

Each air chamber [1] or nostril (see FIG. 4) comprises: a chamber inlet [2] presenting a first perimeter being gradually extended until reaching a second perimeter defining a sensing area [5] adjacent to an area of odor filtration [6], and a system of ventilation [7]; within the interior of the chamber, characteristically between the area of gradual extension of the perimeter and the sensing area, are located fixed splitters [3], preferably comprising 3 plates having different working angles to convert the inlet air flow from laminar to turbulent; preferably, these plates are perpendicular to the air flow and separated one from another. Particularly in the sensing area [5] there are located chemical sensors to differentiate gases and, in the upper part of the same area, there is also located an isolated container [4] for the electronic systems.

Characteristically, the chamber inlet [2] coincides with the ducts of the septum [10] and by means of the ventilation system [7], preferably comprising two fans in opposed directions, one to draw air towards the interior of the system and the other to send it back, the air is inhaled an exhaled into and out of the air chambers [1] in a cyclic manner, that is to say, first one fan is activated to inhale air for a certain time (depending on the characteristics of the environment, for example, windspeed) and is subsequently deactivated, then the contrary fan is activated to exhale air and is subsequently deactivated after a certain time, and the complete process is repeated anew. The inhaled air enters through the ducts [10] of the septum and passes through the inlet [2] of the chamber towards the interior thereof. The inhaled air is sufficiently mixed by means of diverse fixed splitters [3], guiding the air, obliging it to become homogenous and directing it through the air chamber, carrying solely a small sample to the zone whereat the gas sensors are located, denominated sensing area [5]. In this zone there is required at least 1 chemical sensor to differentiate gases and at least 3 chemical sensors of the same type to obtain an average of the responses thereof in order that the measurement be more representative. The remainder of the air is divided by the splitters [3], passing through the air chambers [1] without coming into contact with the sensing area [5].

The sensing area [5] in each air chamber [1] comprises a compartment in the air chamber [1] and a container [4] with the corresponding electronic systems isolated from the sensing area [5], wherein solely the array of sensors is in contact with this hermetically sealed area [5]. The electronic systems comprise voltage regulators for the correct supply to the sensors and the components necessary to realize the acquisition of the electric signals from the sensors and to send them wirelessly towards a processor, normally a computer, realizing the analysis of the data and containing the direction wherefrom the smell emanates.

By virtue of the ventilation system [7] the inhalation process, in addition to carrying the air through the septum [8] and all the areas of the air chamber [1], removes the air from the chamber towards the exterior through the posterior part of the nostril, passing firstly through the area of smell filtration [6], which may comprise a duct or part filled with a material, preferably granular activated carbon on grilles, reacting chemically and absorbing the smells on the passage thereof through it; in this manner the air initially inhaled having a smell exits anew to the environment transformed into clean air. The process of exhalation cleans the air chamber [1] carrying clean air from the exterior through the ventilation system [7], anew passing through the filtration system [6] to clean any particle of smell which it might contain. The air now passes in the inverse direction through the area of sensing [5], of conduction and homogenization or fixed splitters [3], through the inlet of the chamber [2] and the ducts of the septum [10] towards the exterior, preparing the air chamber [1] for a further measurement cycle.

On the basis of these measurements the processor, preferably a computer, can determine through the difference in concentration existing between the nostrils [1] the direction wherefrom the smell analyzed emanates and display it on screen by means of a graphical interface. Having obtained this result, techniques and algorithms may be utilized in order to optimize the trajectory which the mechanism must follow whereto this artificial olfactory system is attached. One of the techniques to determine the direction of the smell is the gradient differential. Consequently, the artificial olfactory system has areas of application in mobile robotics, the detection of sources of smell, such as, for example, detection of leaks of toxic gases, location of explosives, search and rescue of injured persons in disaster zones, to mention some examples.

Furthermore, on utilizing at least one septum [8] having 2 concave inlets [9] the direction wherefrom the smell emanates may be obtained by virtue of the fact that on inhaling the air the impact of the odor molecules on the septum [8] is concentrated in the center of the inlets [9] by virtue of the parabolic concave shape thereof, depending on the direction wherefrom the smell emanates. Consequently, differences in smell concentration are generated in each nostril [1]. Having this information, the processing of the data is realized and the direction of the smell is obtained; in addition, the process of inhalation permits that the concentration from a specific area of the environment reaches the sensors in the sensing area [5] and by means of the splitters [3] solely a homogenous sample arrives, by virtue whereof a more representative measurement of the same environment is obtained. During this process the air containing odor molecules entering through the front is homogenized, is sampled, is measured and, on exiting, passes through the smell filter [6] to be expulsed as clean air towards the external environment without saturating it, such that it is not modified during the process and does not affect the following measurement. In the same manner, on realizing the process of exhaling the air, a quantity of air enters through the posterior part from the external environment, passing in the inverse direction through the system of odor filtration [6], such as to anew arrive clean at the air chamber [1] and the sensing area [5], in this manner desaturating the sensors.

Figure 6:
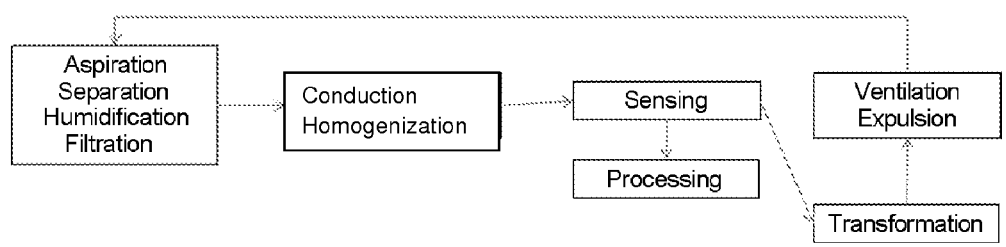
FIG. 6. Flow diagram of the processes realized by the artificial olfactory system.
Figure 7:
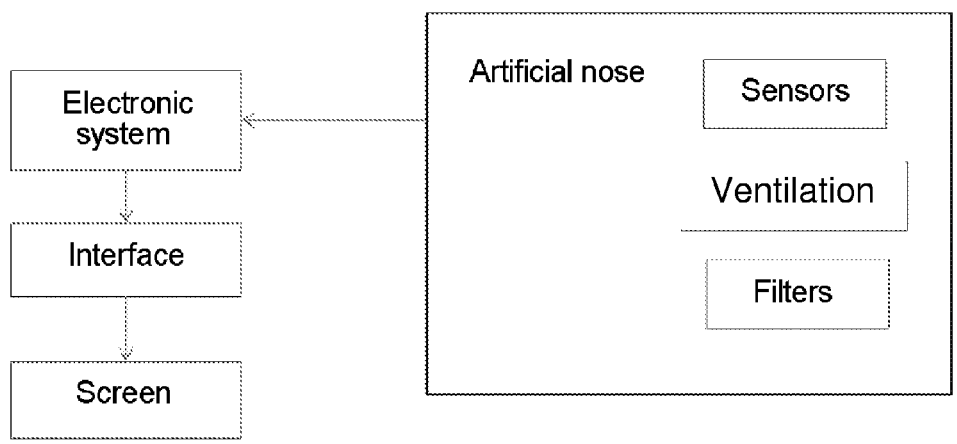
FIG. 7. Schematic diagram of the elements comprising the olfactory system.

For the operation thereof, the method of the olfactory system is supported on the systems of division of the air, ventilation, conduction, homogenization, filtration and transformation of smells, wherein said method is represented in FIG. 6, comprising the following stages:

a) Ventilation/aspiration; the smell from the external environment is carried by an air current generated by the artificial olfactory system towards the interior of the system. This system makes the air containing a smell pass through the subsequent stages until being expulsed through the posterior part of the nostril [1] to the exterior;

b) Division of the air; having aspired the air in stage a), it is drawn towards two or more air inlets [10] corresponding to the number of nostrils [1] in the system and by means of a divider or septum [8] the division of the air flow by zones in the environment is realized, obtaining samples from different positions simultaneously; optionally, following stage b) there may be included a stage of humidification consisting in that in the concave air inlets [9] of the system there is a humidification process which may comprise a material generating humidity, for example, a damp sponge. This humidity generates magnification of the smells, that is to say they are intensified;

c) Particle filtration; the air obtained from stage b) is directed towards the air inlets [9] of the system which, in an optional manner, may utilize a filter, preferably an air filter of foam or cotton to prevent dust particles from entering the system;

d) Homogenization; the air filtered in stage c) passes the fixed splitters [3], which block the air flow, transforming it from laminar to turbulent. In this manner, whilst the air is carried towards the interior of the chamber [1] it is being mixed, becoming homogenized;

e) Directing; solely a required quantity of homogenized air from stage d) is directed towards the sensing area [5] by means of the splitters [3], whilst the remainder of the air passes towards the air chamber to be expulsed towards the exterior without passing the sensors;

f) Sensing; the homogenized sample from stage d) is perceived in the sensing area [5], there being obtained a signal or measurement, this being preprocessed by the electronic circuits isolated in the container [4]; solely the gas sensors are in direct contact with the air sample;

g) Signal processing; the electronic circuits isolated in the container [4] send the signal obtained in stage f) to a processor, preferably wirelessly, to a computer which analyses the signal, processes it and by means of different algorithms obtains the direction wherefrom the smell emanates;

h) Smell transformation or filtration; air entering and exiting through the posterior part of the olfactory system is passed through a smell filter [6], that is to say, through a system which absorbs the odors or transforms them such that the air which is sent to the exterior following being sensed does not contain smell particles and, similarly, that entering the system in the process of exhalation enters clean and desaturates the sensors;

i) Ventilation/expulsion; air from the exterior enters the air chamber by means of the ventilation system [7] in inverse direction, that is to say from the posterior part of the nostril [1] passing therethrough, through the stage of smell filtration h), towards the sensing zone [5], desaturating the sensors, until being expulsed by the septum [8];

j) Return to stage a), whilst the system is in operation.

The process being carried out in a cyclic manner within each of the nostrils [1] is advantageous, by virtue of the fact that it optimizes the measurement through the obtainment of a more representative sample of the environment and is inspired by the natural biological system. Furthermore, on utilizing a complete nose (at least two nostrils [1] and one septum [8]) the direction wherefrom the smell emanates may be calculated, rendering the algorithms of localization of sources of smell simpler.

Having adequately described the present invention, considered to be novel, the content of the following clauses is consequently claimed as exclusive property:

1. The artificial olfactory system, wherein the system comprises a device denominated artificial nose, comprising at least an air chamber, a septum, preferably joined to the air chamber, wherein each air chamber in turn comprises an inlet to the chamber, fixed splitters, a sensing area, a container for the electronic systems, a smell filtration area and a ventilation system.

2. The artificial olfactory system as claimed in claim 1, wherein the artificial nose is of non-porous material, preferably plastic.

3. The artificial olfactory system as claimed in claim 1, wherein the septum is a single part, presenting the geometry similar to that of a human nasal septum, comprising at least two concave inlets and a divider therebetween permitting that the air be concentrated in the central zone of each of the inlets and that the sample of air most representative of the environment in that position be obtained.

4. The artificial olfactory system as claimed in claim 1, wherein the concave inlets of the septum in the interposition thereof present channels denominated ducts of the septum passing completely through the septum.

5. The artificial olfactory system as claimed in claim 1, wherein the inlets of the chambers coincides with the ducts of the septum and by means of the ventilation system is responsible for inhaling and exhaling the air into and out of the air chambers.

6. The artificial olfactory system as claimed in claim 1, wherein the fixed splitters transform the air flow from laminar to turbulent and comprise preferably 3 plates perpendicular to the air flow, separated one from another, and in turn presenting different working angles.

7. The artificial olfactory system as claimed in claim 1, wherein the sensing area requires at least 1 chemical sensor to differentiate gases and at least 3 chemical sensors of the same type to obtain an average of responses in order that the measurement be representative.

8. The artificial olfactory system as claimed in claim 1, wherein the sensing area comprises a compartment in the air chamber isolated from a container containing the corresponding electronic systems.

9. The artificial olfactory system as claimed in claim 8, wherein the electronic systems are isolated from the air chamber, and where in solely the array of sensors is in contact with the compartment of the air chamber hermetically sealed.

10. The artificial olfactory system as claimed in claim 8, wherein the electronic systems comprise voltage regulators for the correct supply to the sensors.

11. The artificial olfactory system as claimed in claim 8, wherein the acquisition of the electric signal from the sensors is preferably transmitted wirelessly to a processor realizing the analysis of the data and obtaining the direction wherefrom the smell emanates.

12. The artificial olfactory system as claimed in claim 1, wherein the ventilation system comprises preferably two fans in opposed directions, one to draw air towards the interior of the system and another to send it back.

13. The artificial olfactory system as claimed in claim 1, wherein the smell filtration area comprises a material, preferably granular activated carbon on grilles, reacting chemically, absorbing the smells when they pass across it in such manner that the air inhaled or exhaled initially having a smell exits or enters transformed anew into clean air.

14. The artificial olfactory system as claimed in claim 11, wherein the processor determines, by means of the difference in concentration existing between the nostrils, the direction wherefrom the smell analyzed emanates; furthermore, techniques and algorithms are utilized to optimize the trajectory which must be followed by the mechanism to which the artificial olfactory system is attached.

15. The artificial olfactory system as claimed in claim 14, wherein one of the techniques to determine the direction of the smell is the gradient differential.

16. The method of operation of the artificial olfactory system as claimed in claim 1, wherein the method comprises the following stages:
   a) Ventilation/aspiration;
   b) Division of the air;
   c) Particle filtration;
   d) Homogenization;
   e) Directing;
   f) Sensing;
   g) Signal processing;
   h) Smell transformation or filtration;
   i) Ventilation/expulsion;
   j) Return to stage a).

17. The method of operation of the artificial olfactory system as claimed in claim 16, wherein in stage a) the smell from the external environment is carried by a current of air generated by the artificial olfactory system towards the interior of the system, making it pass through the subsequent stages of the method until expulsion thereof through the posterior part of the nose to the exterior.

18. The method of operation of the artificial olfactory system as claimed in claim 16, wherein in stage b) the air aspired in stage a) is drawn towards two or more air inlets corresponding to the number of nostrils in the system, by means of the septum the division of the air flow being realized by zones in the environment, obtaining samples from different positions simultaneously.

19. The method of operation of the artificial olfactory system as claimed in claim 16, wherein subsequent to stage b) and prior to stage c) optionally, in the air inlets of the system, the inlet air is humidified by means of a material generating humidity, for example a damp sponge, this humidity generating magnification of the smells, that is to say they are intensified.

20. The method of operation of the artificial olfactory system as claimed in claim 16, wherein in stage c) the air obtained from stage b) is directed to the air inlets of the system and that optionally an air filter may be utilized, preferably of foam or cotton, to prevent dust particles from entering the system.

21. The method of operation of the artificial olfactory system as claimed in claim 16, wherein in stage d) the filtered air from stage c) passes the fixed splitters blocking the air flow, transforming it from laminar to turbulent, in this manner whilst the air is carried towards the interior of the chamber it is being mixed, becoming homogenized.

22. The method of operation of the artificial olfactory system as claimed in claim 16, wherein in stage e) solely a required quantity of homogenized air from stage d) is directed towards the sensing area by means of splitters, whilst the remainder of the air passes towards the air chamber to be expulsed towards the exterior without passing the sensors.

23. The method of operation of the artificial olfactory system as claimed in claim 16, wherein in stage f) the homogenized sample from stage d) is perceived in the sensing area, obtaining a signal or measurement being preprocessed by the electronic circuits isolated in the container, solely the gas sensors being in direct contact with the sample.

24. The method of operation of the artificial olfactory system as claimed in claim 16, wherein in stage g) the electronic circuits send the signal obtained in stage h) to a processor, preferably wirelessly to a computer, analyzing the signal, processing it and, by means of different algorithms, obtaining the direction wherefrom the smell emanates.

25. The method of operation of the artificial olfactory system as claimed in claim 16, wherein in stage h) on air entering through the posterior part of the olfactory system, it passes through a smell filter, is to say through a system which absorbs the smells or transforms them in such manner that the air sent out of the system subsequent to being sensed has no smell particles and, similarly, that entering the system in the process of exhalation enters clean and desaturates the sensors.

26. The method of operation of the artificial olfactory system as claimed in claim 16, wherein in stage i) the air enters the air chamber by means of the ventilation system in inverse direction, that is to say from the posterior part of the nostril, passing therethrough, through the stage of smell filtration h), towards the sensing zone, desaturating the sensors, until being expulsed through the septum.

27. The method of operation of the artificial olfactory system as claimed in claim 16, wherein in stage j) return is made to stage a), whilst the system is in operation.

* * * * *